United States Patent [19]

Parker et al.

[11] Patent Number: 4,580,233

[45] Date of Patent: Apr. 1, 1986

[54] METHOD OF MEASURING MOISTURE CONTENT OF DIELECTRIC MATERIALS

[75] Inventors: Robert S. Parker; Frank C. Beall, both of Puyallup, Wash.

[73] Assignee: Weyerhaeuser Company, Tacoma, Wash.

[21] Appl. No.: 421,624

[22] Filed: Sep. 22, 1982

[51] Int. Cl.[4] .................. G01N 25/56; G01R 27/26
[52] U.S. Cl. .................................... 364/550; 73/73; 324/61 R; 364/482
[58] Field of Search ............... 73/73, 74; 324/61 R, 324/61 P; 364/550, 482

[56] References Cited

U.S. PATENT DOCUMENTS

| | | | |
|---|---|---|---|
| 3,124,430 | 3/1964 | Eicken | 73/73 |
| 3,155,898 | 11/1964 | Chope | 324/61 R |
| 3,155,899 | 11/1964 | Davidson | 324/61 R |
| 3,155,900 | 11/1964 | Hanken | 324/61 R |
| 3,155,902 | 11/1964 | Walls | 324/61 R |
| 3,241,062 | 3/1966 | Baird | 324/61 R |
| 3,249,865 | 5/1966 | Hanken | 324/61 R |
| 3,255,412 | 6/1966 | Ko-Hsin | 324/61 R |
| 3,320,946 | 5/1967 | Dethloff et al. | 324/61 R X |
| 3,323,045 | 5/1967 | Baird | 324/61 R |
| 3,323,047 | 5/1967 | Martin et al. | 324/61 R |
| 3,339,137 | 8/1967 | Perry | 324/61 R |
| 3,354,388 | 11/1967 | Perry | 324/61 R |
| 3,443,219 | 5/1969 | Adams | 324/61 R |
| 3,496,460 | 2/1970 | Martin | 324/61 R |
| 3,504,280 | 3/1970 | Byrd | 324/61 R |
| 3,559,052 | 1/1971 | Fathauer | 324/61 R |
| 3,807,055 | 4/1974 | Kraxberger | 324/61 R X |
| 4,058,766 | 11/1977 | Vogel et al. | 324/61 R |
| 4,259,633 | 3/1981 | Rosenau | 324/61 R X |
| 4,399,404 | 8/1983 | Resh | 73/73 X |

OTHER PUBLICATIONS

*Water in Wood* by C. Skaar, Syracuse University Press, Syracuse, N.Y., 1972, pp. 35–53.

Primary Examiner—Errol A. Krass
Assistant Examiner—Edward R. Cosimano

[57] ABSTRACT

The present invention is a method for measurement of moisture in dielectric materials. It is particularly useful for lumber. In the preferred version, at least two alternating current signals whose frequencies differ by a factor of at least 10 are capacitively coupled to the material. The coupling electrodes are in bridge circuits whose unbalance is measured at each frequency. The temperature of the dielectric material is also determined. Bridge unbalance signals are separated and rectified and the voltages, as well as a temperature analog voltage, are entered into a microprocessor programmed with a suitable algorithm to calculate a temperature corrected moisture value. The method overcomes significant inaccuracies in moisture readings due to temperature dependency.

48 Claims, 5 Drawing Figures

METHOD OF MEASURING MOISTURE CONTENT OF DIELECTRIC MATERIALS

BACKGROUND OF THE INVENTION

The present invention relates to the measurement of moisture in materials which broadly could be considered as dielectric in their propeties. More specifically, it relates to the determination of moisture by measurement of the impedance of the dielectric material at differing alternating frequencies. Provision is made for correcting errors introduced because of temperature variation and variation in the nature of the dielectric material itself. The method is particularly well adapted for measurement of the moisture content of wood.

It is important to control the moisture content of many materials having dielectric properties. Grain can serve as one example. If the moisture content of stored grain is too high, mold growth and ultimate spoilage can result. Wood is another material in which moisture should desirably be controlled within specified limits which depend upon the ultimate application. Wood intended for construction framing should desirably have a moisture content below 20% to minimize fungal attack. Finish lumber, such as that used for trim and moldings, normally is specified with moisture contents at or near those which will be in equilibrium with the ultimate environment. This is typically in the 7–10% range. Wood which is to be adhesively bonded or laminated is normally dried to moisture contents of 12% or below.

Through the years, a number of nondestructive moisturemeasuring methods have been developed. Most of these depend upon some electrical property of the material being measured. The earliest instruments for measuring the moisture content of wood determined its electrical resistivity by passing a direct current through it. Handheld moisture meters were soon developed so that moisture content could be readily estimated in either the manufacturing plant or in the field where the product was being used. These normally comprise a pair of pins or needles of predetermined size and spacing which are driven into the wood along the grain direction. The needles are connected to a direct current source and a megohmeter, which is precalibrated to give a direct estimate of moisture content. Similar meters have been developed for measurement of the moisture in many other materials.

Another type of meter was developed somewhat later that did not depend on making direct contact with the material. These are typically capacitively coupled. They are suitable for use on conveyor lines in a manufacturing plant, and are often used in conjunction with ancillary equipment which can mark or reject high moisture samples for later redrying. Internal impedance is the property most commonly measured. In many cases the internal resistance is by far the most important component of the impedance. Thus, many of the noncontact meters are similar to the direct-current meters in their use of resistivity to estimate of moisture content.

In the case of wood, resistivity is an almost ideal parameter to measure because of its great variation with relatively small differences in moisture content. The resistance of Douglas-fir at 27° C., using needle electrodes 3.1 cm apart and driven into a depth of 0.8 cm, drops from about 22,400 megohms at 7% moisture content to 0.60 megohms at 24% moisture. Accuracy below this moisture range begins to fall off because of the difficulties in measuring very high resistances. Accuracy also is decreased as the fiber saturation point of the species is approached. No satisfactory instrumental method is yet in use for accurate estimation of moisture content of solid wood members above the fiber saturation point.

The noncontact moisture meters vary considerably in their mode of operation. The most common ones for measuring the moisture content of a dielectric material capacitively couple the material into one arm of a bridge circuit. The bridge unbalance is then measured as two alternating frequencies are impressed across the bridge, either simultaneously or sequentially. These alternating current signals are then filtered into the original component frequencies and rectified to produce DC analog signals. The resultant voltages are a function of the ratio of change in voltage drop across the test capacitor which correspond to each frequency, when the material being tested is located between the plates of the capacitor. Most typically, the estimated moisture content is calculated from the analog voltages by dividing the higher frequency component by the lower frequency component with the inclusion of appropriate constants. Exemplary meters of this type are shown in the patents to Davidson U.S. Pat. No. 3,155,899; Walls U.S. Pat. No. 3,155,902; Baird U.S. Pat. No. 3,241,062; and Liu U.S. Pat. No. 3,255,412.

In U.S. Pat. No. 3,155,902, Walls notes a number of deficiencies in capacitively-coupled moisture meters. A number of these relates to the internal stability and calibration of the electronic component. Two others are a result of uncontrolled outside influences. Walls notes that the measurement is not independent in the position of material between the capacitor plates. He further notes that the measured moisture content has a temperature dependency. However, the inventor offers no solutions for either of these problems. Perry, in U.S. Pat. No. 3,339,137 and 3,354,388, shows a noncontact meter that overcomes the position problem by using opposed electrodes having a fieldfree region between them. His electrodes are at equal voltage and polarity. This system provides compensation for positioning and it is essentially immaterial where the dielectric is located in the void space between the electrodes, Baird, in U.S. Pat. No. 3,241,062, shows a relatively complex system of temperature compensation. This involves a sensor and associated circuitry which uses a servomotor to adjust a series of potentiometers controlling the output voltage of one of the oscillators. A major problem with this system is the lag time associated with electromechanical system.

One problem appears to be as yet unaddressed. A given moisture meter is normally calibrated so as to work only on a specific dielectric material. Even in the measurement of wood moisture content there is uncompensated variation from species to species. Meters are normally calculated on the basis of coastal Douglas-fir. If, for example, a meter so calibrated is used on pine or hemlock, somewhat different moisture readings will be indicated even though the moisture content of all samples is identical.

The present ivention comprises a method for measuring the moisture content of dielectric materials which has an internal electronic compensation for the temperature and nature of the dielectric material being measured. It is of the general type which employs a plurality of alternating current signals of different frequencies impressed across a bridge circuit into which the sample material is capacitively coupled.

SUMMARY OF THE INVENTION

The present invention is a method of measuring the moisture content of a moisture-containing dielectric material. This is accomplished by capacitively coupling the material into at least one bridge circuit and measuring the resulting bridge unbalance at each frequency when an alternating current having at least two superposed frequencies is applied across each bridge circuit. Within the restrictions imposed by the current state of the art in electronic circuitry, any number n of superposed alternating current frequencies may be applied across the bridge, where n is equal to or greater than 2. Normally two frequencies will give excellent results although resolution is improved with higher numbers of frequencies. The bridge unbalance is determined at each frequency and the AC unbalance voltage at each frequency is converted into a direct-current voltage signal. Simultaneously, the temperature of the material is measured. The direct-current voltages and the voltage analog of the temperature are entered into an algorithm of the following form which can then be solved to display a temperature-corrected moisture content $$MC = A_0(T) + \sum_{i=1}^{n} B_i(T) V_i + \sum_{i=1}^{n} \sum_{j=1}^{n} C_{ij}(T) V_i V_j$$

where MC is moisture content, $A_0(T)$, $B_i(T)$, and $C_{ij}(T)$ are all polynomial functions of temperature where n is a whole number equal to or greater than 2, and $V_i$ and $V_j$ are the direct current amplitudes of the ith and jth frequency components.

Accuracy is improved when there is a significant separation between each of the frequencies employed. When only two frequencies are used, it is desirable that they be different by at least a factor of 10. With wood as a dielectric material, excellent results are obtained when the lowest frequency is equal to or less than 1 kHz and the higher frequency is equal to or greater than 10 kHz.

The algorithm to determine moisture content may be solved manually, but it is preferred that the data be entered into a computer such as a microprocessor which gives moisture content as an output on any convenient type of display system.

The nature of the dielectric material will affect the indicated moisture content. Regardless of the material used to calibrate the meter initially, it is within the scope of the present invention to provide simple equations which can compensate for the particular dielectric being measured. For example, appropriate algorithms can be programmed into a microprocessor to correct the initially computed temperature corrected moisture on a given dielectric substance to an actual moisture value, even though the meter was originally calibrated on another dielectric material.

A preferred method uses at least one measuring head in which a pair of coupling electrodes are arranged in a side-by-side relationship. Each electrode is in parallel with a capacitor in one leg of a bridge circuit, with a separate bridge circuit being supplied for each electrode. These bridge circuits are provided in a balanced push-pull arrangement. For many types of dielectric material; e.g., lumber, it is desirable to supply a plurality of measurement heads in a parallel arrangement. In this way the material is sampled at a number of locations. Circuitry can be supplied so that each individual head can give a moisture readout, or the readouts from the heads may be averaged. The latter method is the one that will normally be used, although individual readouts can supply an indication of moisture variation within any given sample.

The method of the present invention will often be used when the material being measured is passing by a series of heads arranged above a conveyor line. To again use the example of lumber, the moisture content of each board will be individually measured. Boards in which the moisture content is above or below a preset range can be mechanically rejected from the line or printed with an indicator dye so that they can be manually removed at some remote location.

Where the sensing heads are located over a conveyor line which is transporting individual dielectric objects to be metered it is convenient to have a detection means in advance of the heads which signals that a new sample is entering the metering zone. Where the samples are of variable size, such as is typical of lumber in a sawmill, a material detection means may be present before each metering head in the assembly. In this way, the circuitry can be arranged so that only those heads which will be fully coupled to the material will be activated. Any heads which are not fully coupled can be disabled or deactivated in some manner so that their outputs do not enter into an averaged value.

It is further beneficial to include a second material detection means immediately following the measuring heads to indicate when the material has moved from the zone in which is it effectively coupled to the heads. This means can send a signal to the microprocessor indicating that the sample has moved from the measuring zone, whereupon the microprocessor can be electronically reset to be ready for measuring the next object which enters the metering zone.

It has been found that when a side-by-side electrode arrangement is used in which the electrodes form part of a capacitive leg of balanced individual bridge circuits, the meter is relatively insensitive to variations in distance between the electrodes and material being measured.

It is an object of the present invention to provide a method for measuring the moisture content of moist dielectric materials which has improved accuracy over methods hereto available.

It is another object to provide a method for measuring the moisture content of dielectric materials which compensates automatically for the temperature of the material being measured.

It is a further object to provide a noncontact method of measuring moisture content of materials which is tolerant of variations in the distance between the material and the measuring head.

It is yet another object to provide a method for measuring the moisture content of materials which provides compensation for the dielectric characteristics of the specific material being measured.

It is still another object to provide a method for accurately measuring the moisture content of individual discreet objects passing by a metering station located adjacent to a conveyor line.

These and many other objects will become readily apparent upon reading the detailed description of the invention when taken in conjunction with the attached drawings.

DETAILED DESCRIPTION OF THE PREFERRED EMBODIMENTS

The following detailed description will use wood as an example of a dielectric material whose moisture content is being measured. It will be apparent to one skilled in the art that the method to be described would be suitable for many different types of dielectric materials which tend to absorb moisture. Among these might be grains, starches, sugar, tobacco, fabrics of various types, etc.

Figure 1:
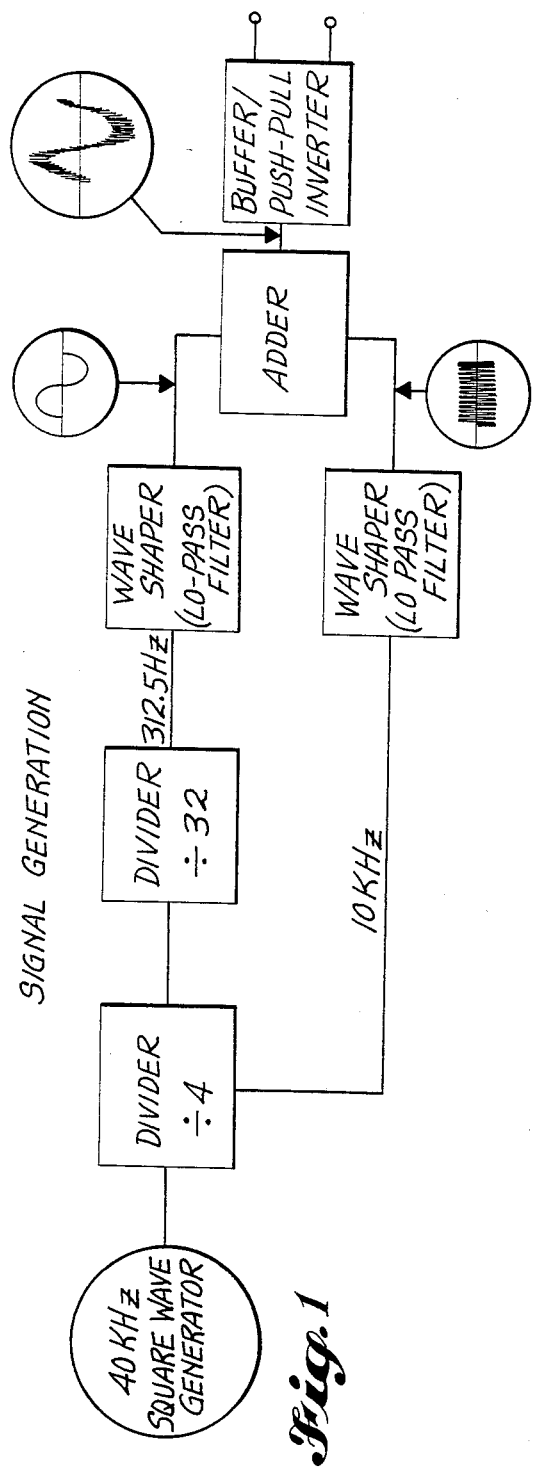
FIG. 1 is a block diagram showing the signal generation section of the moisture meter.

Reference to FIG. 1 shows the signal generation section of the moisture meter. The single oscillator employed is a 40-kHz square wave generator. A signal is sent through a first divider which divides the signal produced by a factor of four to produce a 10 kHz output signal. The 10 kHz signal is split and a portion serves as the input to a second divider which divides by a factor of 32 to produce an output having a frequency of 312.5 Hz. Both the 10 kHz and the 312.5 Hz signals are directed to wave-form shapers which remove the harmonic content and deliver an output wave form which is essentially sinusoidal. The wave form shapers are basically low-pass filters designed to pass the selected frequencies. The output of each of the low-pass filters is trimmed to provide a 10-volt peak-to-peak signal. These two signals are then combined in an adder to produce a complex wave which is now 20-volts peak-to-peak. The combined frequencies are finally passed through a buffer/phase inverter which delivers a push-pull output signal to the measuring bridges.

Figure 2:
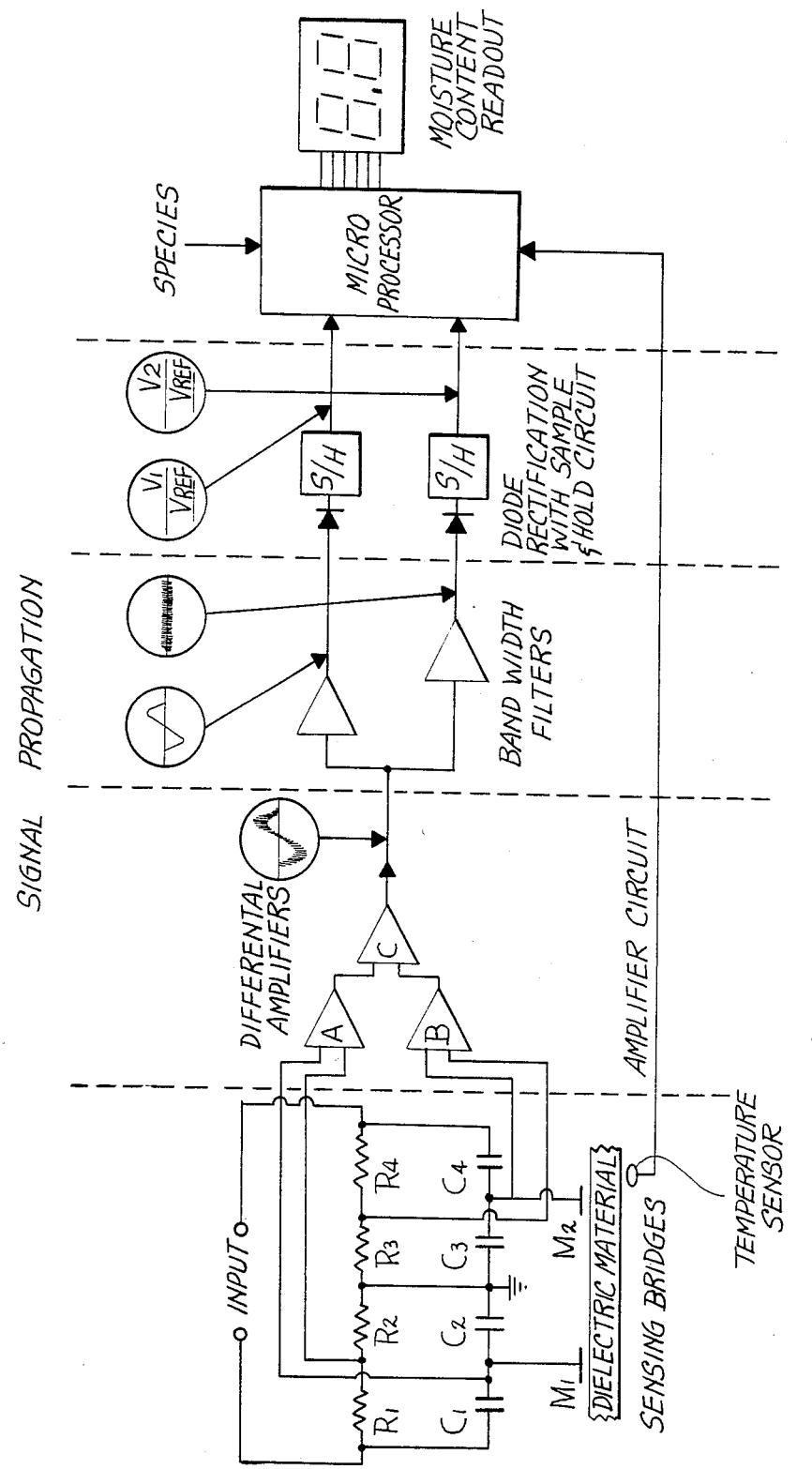
FIG. 2 is a block diagram showing the metering bridges and the signal processing section of the meter.

The output from the signal-generating section is delivered to two push-pull bridge circuits. As seen in FIG. 2, the first bridge comprises resistors $R_1$ and $R_2$ on one side of the bridge and capitators $C_1$ and $C_2$ on the other side of the bridge. The second bridge circuit comprises equivalent resistors $R_3$ and $R_4$ on one side and capacitors $C_3$ and $C_4$ on the other side. Measuring electrode $M_1$ is arranged in parallel with capacitor $C_2$, while measuring electrode $M_2$ is in parallel with capacitance $C_4$. The output of the first bridge is entered the first of a matched pair of differential amplifiers, here designated A. The output of the second bridge enters an equivalent differential amplifier B. The output of these differential amplifiers forms the input for a third differential amplifier designated C. The output of amplifier C will still be a complex wave form containing components from the original 10 kHz and 312.5 Hz input signals. The individual components at each frequency will reflect the unbalance in the bridge circuits respectively caused by the 10 kHz and 312.5 Hz input signals.

The output of the final differential amplifier is directed to a pair of filters which separate the individual frequency components from the complex alternating current wave. The results are again individual signals at 10 kHz and 312.5 Hz which are not somewhat diminished over their original amplitude. These are now rectified to produce direct current voltages which can be continuously compared with DC reference voltages reflecting a balanced condition. The DC currents are now directed through sample and hold circuits from which point they enter a microprocessor.

There are normally two other inputs into the microprocessor. One is from a temperature sensor which determines the temperature of the material being measured. This sensor can be a thermistor, infrared detector, or one of the other sensing means well known in the art. Its output is typically a voltage analog. Finally, another input to the microprocessor is an analog voltage signal related to the nature of the dielectric material being measured. In the case of wood, this will normally be the species. The microprocessor is programmed with an algorithm that processes the input information and sends a signal to an output device which indicates the moisture content of the material.

The generalized algorithm has the form $$MC = A_0(T) + \sum_{i=1}^{n} B_i(T) V_i + \sum_{i=1}^{n} \sum_{j=1}^{n} C_{ij}(T) V_i V_j$$

where MC is moisture content, $A_0(T)$, $B_i(T)$, and $C_{ij}(T)$ are all polynomial functions of temperature, n is a whole number equal to or greater than 2, and $V_i$ and $V_j$ are the direct current amplitudes of the ith and jth frequency components.

This generalized algorithm covers the situation where n superposed alternating current frequencies are applied across the measuring bridges. In most cases, such as the one just described, n will be equal to 2. When n=2, the algorithm may be simplifed to the form $$MC = a + bV_1 + cV_2 + dV_1V_2$$

where MC is moisture content, $V_1$ and $V_2$ are the direct current voltage signals, and the coefficients are temperature dependent according to their relationships $$a = \sum_{i=0}^{m} a_i T^i; \; b = \sum_{i=0}^{m} b_i T^i; \; c = \sum_{i=0}^{m} c_1 T^i; \text{ and } d = \sum_{i=0}^{m} d_1 T^i$$

with m being a whole number equal to or greater than 1.

Unless extreme accuracy of measurement is required, for most purposes first-order approximations of the coefficients may be made as follows where $a = a_0 + a_1 T$, $b = b_0 + b_1 T$, $c = c_0 + c_1 T$, and $d = d_0 + d_1 T$, where T is the temperature of the material being measured.

Coastal Douglas-fir is the reference wood by which most moisture meters are calibrated. For a meter constructed using the previously described circuitry, the algorithm coefficients for Douglas-fir are as follows:

| | | | |
|---|---|---|---|
| $a_0 =$ | 1.4 | $a_1 =$ | 0.0326 |
| $b_0 =$ | 33.7 | $b_1 =$ | 0.346 |
| $c_0 =$ | 6.13 | $c_1 =$ | −0.0198 |
| $d_0 =$ | −16.1 | $d_1 =$ | 0.141 |

For any particular meter construction, the coefficients of the algorithm can be determined experimentally by the measurement of dielectric materials having known moisture contents at some predetermined temperature. The temperature may be determined in a number of ways. Where the dielectric has been in a given ambient environment for a sufficient time to attain temperature equilibrium, simply measuring the ambient temperature will be sufficient. Otherwise, conventional measuring instruments can be used to determine the temperature of each sample.

Figure 3:
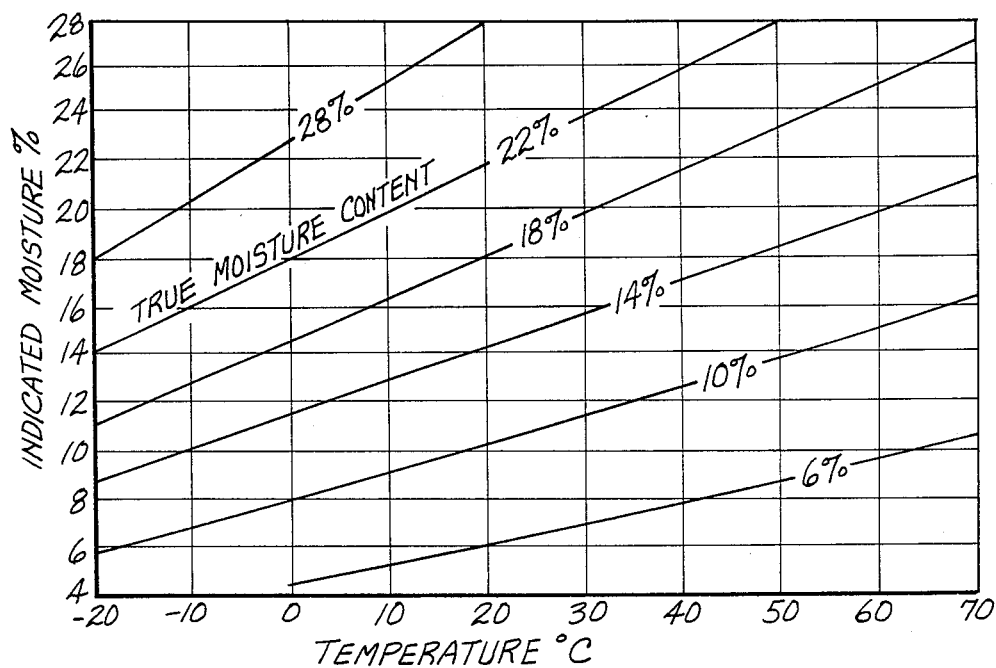
FIG. 3 is a graph showing the variation in apparent moisture content with changes in temperature.

Reference to FIG. 3 shows the error that can be introduced in conventional D.C. resistance moisture readings of wood by failure to account for temperature. This figure is adapted from a chart now widely used in the industry, but it should be considered only an approximation at best. As one example, wood which is to be adhesively bonded to form laminated structural beams generally should have a moisture content of 12% or below. Referring to FIG. 3, wood at 12% true moisture, measured at 20° C., would be acceptable for laminating. If the same wood was measured warm, as at the unstacker following kiln dryers, the indicated moisture kiln content would be considerably higher. When measured at 60° C., the indicated moisture would be about 17.5% even though the actual moisture was 12%. Without a correction being applied, this wood would be unnecessarily rejected as being too wet. To date, it has been so awkward to apply temperature corrections where the sample population literally consists of hundreds of thousands of boards, that it has not been practical to apply an effective form of temperature correction of moisture readings. The forementioned U.S. Pat. No. 3,241,062 to Baird is apparently the only device which attempted to incorporate automatic temperature correction and, for whatever reasons, it has apparently never been commercially produced. The device employing the presently described method appears to be a major step forward in improving the accuracy of moisture determination by automatic, near instantaneous correction of the temperature dependence problem.

The matter of the nature of the dielectric material being measured is another problem which has received very little attention. As mentioned before, moisture meters for wood are normally calibrated on coastal Douglas-fir. The person who wished to use these meters on other species was at some risk of obtaining inaccurate values because of the known differences in dielectric properties between woods of different species. It is readily within the skill of the art to program the microprocessor so that information on the species being measured can be entered simply be setting a switch, or some similar device, to the proper setting. A linear approximation can be used to give a species correction adequate for all practical purposes. This is of the form $$MC_{corr} = k_1 + k_2 MC$$

where the coefficients $k_1$ and $k_2$ may readily be determined experimentally by measuring wood of different species having known moisture contents. For coastal Douglas-fir, the coefficient $k_1$ is 0 and $k_2$ is 1, so that the slope of the curve is unity. For most other commercially important wood species, the coefficient $k_1$ will fall in the range between 4 and 10 and $k_2$ will lie between 0.5 and 1.2.

Figure 4:
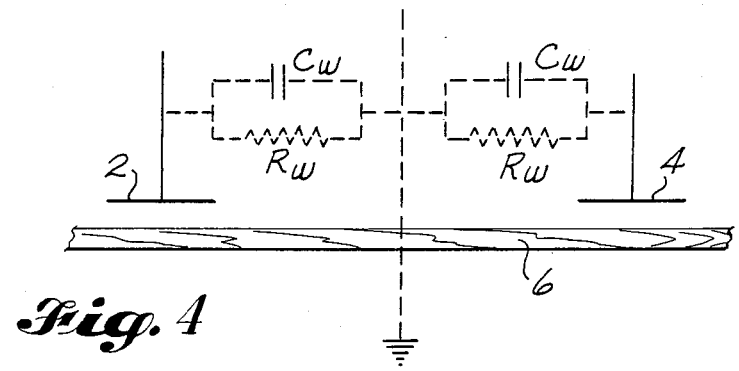
FIG. 4 shows the electrical equivalent of the sample as it is seen by the measuring electrodes.

A noncontact capacitively-coupled moisture meter of the type utilized in the present method can normally be used to measure moisture contents from about 4% up to approximately 28%. Somewhat less accuracy will be experienced at the extreme ends of this range. This is true also of resistance-type meters. While the noncontact meter will actually measure the capacitive reactance of the dielectric to which it is coupled, in the above moisture content range the resistance will form the most important component of the reactance. FIG. 4 shows two electrodes 2,4 at opposite instantaneous polarity which are capacitively coupled to a piece of wood 6. When these electrodes are wired as shown in FIG. 2 in a push-pull balanced bridge circuit, they will "see" the wood capacitance and resistance as if it was effectively between the electrode and ground. The effective capacitance of $C_w$ is very small so that its reactance is very large at the frequencies employed. This reactance is also large in comparison with $R_w$. In effect, the meter exemplified herein is actually measuring wood resistance in similar fashion to a D.C. meter having electrodes actually driven into the wood.

Figure 5:
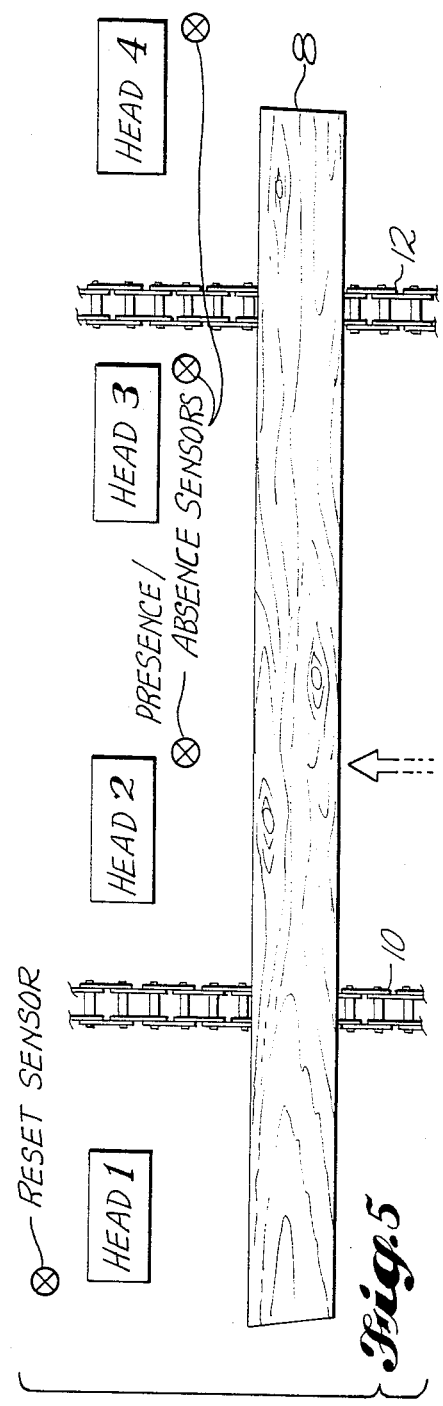
FIG. 5 is a diagrammatic arrangement showing a piece of lumber passing beneath a plurality of sensing heads.

FIG. 5 shows a board 8 being borne on conveyor chains 10,12 and approaching a bank of four metering heads. It is assumed that the left ends of all boards approaching the metering station will be in approximately the same position, as could readily be controlled by a line bar, but that these boards will be of variable length. Three of the four heads has a sensor immediately preceding it to detect whether or not the board will be fully coupled to the head. These sensors can be electrical switches, photocells, or any other well-known type of proximity indicator. Even the electrical output of the head as a board passes could be programmed into the microprocessor as a presence/absence signal.

In the present example, it is assumed that all of the boards will be long enough to engage at least the first head. It is for this reason that a sensor is not required preceeding it. As shown in FIG. 5, heads 1, 2, and 3 will be activated. Head 4 will not be activated since the board is not long enough to be fully coupled to the head; i.e., the material would not be under the full area of the head. This will indicate to the microprocessor that an average moisture content should be calculated only on the basis of the output of the first three heads. Head 4 will either be deactivated or its output will be ignored in the moisture determination. In addition to giving an average moisture reading, the output may be designed to indicate the moisture content from each head in order to give an indication of the uniformity of moisture distribution within the sample. The microprocessor could also be programmed with ancillary equipment so as to automatically reject a board which showed an overly high moisture content at any measuring head. After the board has passed by the heads, the reset sensor will be triggered to indicate to the microprocessor that the next data received will be from a new sample. Information from each sample passing the measuring heads is stored in the sample and hold circuits (FIG. 2) until it is cleared by the approach of a new sample.

Having thus disclosed the best mode known to the inventors of practicing the present process, it will be apparent to those skilled in the art that many variations can be made without departing from the spirit of the invention. It is therefore intended that the scope of the invention be limited only by the following claims.

What is claimed is:

1. A method of measuring the moisture content of a moisture-containing dielectric material by capacitively coupling it into at least one bridge circuit and measuring the bridge unbalance when an alternating current input having superposed frequencies is applied across each bridge circuit, the improvement which comprises:

a. applying n superposed alternating current frequencies to the bridge, where n is a whole number equal to or greater than 2;
b. determining the bridge unbalance caused at each frequency and converting it into a direct current voltage signal;
c. measuring the temperature of the material; and
d. computing the moisture content by entering the voltage signals and temperature into an algorithm having the form:

$$MC = A_0(T) + \sum_{i=1}^{n} B_i(T) V_i + \sum_{i=1}^{n} \sum_{j=1}^{n} C_{ij}(T) V_i V_j$$

where MC is moisture content, $A_0(T)$, $B_i(T)$, and $C_{ij}(T)$ are all polynominal functions of temperature n is a whole number equal to or greater than 2, and $V_i$ and $V_j$ are the direct current amplitudes of the ith and jth frequency components.

2. The method of claim 1 which includes providing a computer which receives inputs of bridge unbalance voltage and temperature and solves the algorithm to indicate a moisture content.

3. The method of claims 1 or 2 in which the lowest and highest frequencies differ at least by one power of 10.

4. The method of claim 3 where the lowest frequency is equal to or less than 1 kHz.

5. The method of claim 3 where the highest frequency is equal to or greater than 10 kHz.

6. The method of claims 1 or 2 in which the moisture content is corrected for the particular characteristics of the dielectric material by entering the uncorrected value into the algorithm $$MC_{corr} = k_1 + k_2 MC$$

where $k_1$ and $k_2$ are coefficients unique to the dielectric material being measured.

7. The method of claim 6 in which the dielectric material is wood.

8. The method of claims 1 or 2 including providing two bridge circuits in a balanced push pull arrangement each bridge circuit having a sensing electrode in parallel with a capacitor in one leg of the bridge circuit, each electrode having an adjacent zone within which it is effectively capacitively coupled to the material being measured.

9. The method of claim 8 in which the coupling electrodes are arranged side-by-side in a measuring head.

10. The method of claim 9 including providing a plurality of measurement heads arranged in parallel.

11. The method of claim 10 including providing conveying means to convey the dielectric material to and from a working proximity with the measuring heads.

12. The method of claim 11 which includes providing material detection means in advance of the heads to determine which heads which will be fully coupled to the dielectric material and to deactivate any heads which are not fully coupled.

13. The method of claim 11 which further includes providing material detection means following the measuring heads to indicate when the material has moved out of the zone in which it is effectively coupled to the heads.

14. The method of claim 12 which further includes providing material detection means following the measuring heads to indicate when the material has moved out of the zone in which it is effectively coupled to the heads.

15. The method of claim 13 in which the dielectric material is wood.

16. The method of claim 14 in which the dielectric material is wood.

17. In the method of measuring the moisture content of a moisture containing dielectric material by capacitively coupling the material into at least one bridge circuit and measuring the bridge unbalance when an alternating current input having two superposed frequencies is applied across each bridge circuit, the improvement which comprises:
a. determining the bridge unbalance caused at each frequency and converting it into a direct current voltage signal,
b. measuring the temperature of the material, and
c. computing the moisture content by entering the voltage signals and temperature into an algorithm having the form $$MC = a + bV_1 + cV_2 + dV_1V_2$$

where MC is mositure content, $V_1$ and $V_2$ are the direct current voltage signals and the coefficients are temperature dependent according to the relationships $$a = \sum_{i=0}^{m} a_i T^i, \; b = \sum_{i=0}^{m} b_i T^i, \; c = \sum_{i=0}^{m} c_i T^i, \text{ and } d = \sum_{i=0}^{m} d_i T^i$$

with m being a whole number equal to or greater than 1.

18. The method of claim 17 in which the algorithm coefficients are first order approximations where $a = a_0 + a_1 T$, $b = b_0 + b_1 T$, $c = c_0 + c_1 T$, and $d = d_0 d_1 T$, where T is the temperature of the material being measured.

19. The method of claims 17 or 18 which includes providing a computer which receives inputs of bridge unbalance voltage and temperature and solves the algorithm to indicate a moisture content.

20. The method of claims 17 or 18 in which the lowest and highest frequencies differ at least by one power of 10.

21. The method of claim 20 where the lowest frequency is equal to or less than 1 kHz.

22. The method of claim 20 where the highest frequency is equal to or greater than 10 kHz.

23. The method of claims 17 or 18 in which the moisture content is corrected for the particular characteristics of the dielectric material by entering the uncorrected value into the algorithm $$MC_{corr} = k_1 + k_2 MC$$

where $k_1$ and $k_2$ are coefficients unqiue to the dielectric material being measured.

24. The method of claim 23 in which the dielectric material is wood.

25. The method of claims 17 or 18 including providing two bridge circuits in a balanced push pull arrangement each bridge circuit having a sensing electrode in parallel with a capacitor in one leg of the bridge circuit, each electrode having an adjacent zone within which it is effectively capacitively coupled to the material being measured.

26. The method of claim 25 in which the coupling electrodes are arranged side-by-side in a measuring head.

27. The method of claim 26 including providing a plurality of measurement heads arranged in parallel.

28. The method of claim 27 including providing conveying means to convey the dielectric material to and from a working proximity with the measuring heads.

29. The method of claim 28 which includes providing material detection means in advance of the heads to determine which heads will be fully coupled to the dielectric material and to deactivate any heads which are not fully coupled.

30. The method of claim 28 which further includes providing material detection means following the measuring heads to indicate when the material has moved out the zone in which it is effectively coupled to the heads.

31. The method of claim 29 which further includes providing material detection means following the measuring heads to indicate when the material has moved out of the zone in which it is effectively coupled to the heads.

32. The method of claim 30 in which the dielectric material is wood.

33. The method of claim 31 in which the dielectric material is wood.

34. A method of measuring the moisture content of moisture containing dielectric material which comprises:
  a. providing at least one pair of electrodes in a coupled relationship with the material;
  b. driving the electrodes with an alternating current signal comprising two superposed frequencies so that opposite electrodes of a pair are at essentially equal voltages of opposite polarity, each electrode being located in an arm of separate bridge circuits;
  c. sensing the unbalance signals in the bridge circuits caused by the presence of the material adjacent to the electrodes, said signals containing components of unbalance at each frequency;
  d. combining the unbalance signals from the two bridges;
  e. separating the combined signal into its individual frequency components and rectifying each component to form direct current voltage signals proportional to the bridge unbalance caused at each frequency;
  f. sensing the temperature of the dielectric materials; and
  g. computing the moisture content by entering the voltage signals and the temperature into an algorithm having the form $$MC = a + bV_1 + cV_2 + dV_1V_2$$

where MC is moisture content, $V_1$ and $V_2$ are the direct current voltage signals, and the coefficients are temperature-dependent according to the relationships $$a = \sum_{i=0}^{m} a_i T^i, \quad b = \sum_{i=0}^{m} b_i T^i,$$

$$c = \sum_{i=0}^{m} c_i T^i, \quad d = \sum_{i=0}^{m} d_i T^i,$$

with m being a whole number equal to or greater than 1.

35. The method of claim 34 in which the algorithm coefficients are first order approximations where $a = a_0 + a_1T$, $b = b_0 + b_1T$, $c = c_0 + c_1T$, and $d = d_0 + d_1T$, where T is the temperature of the material being measured.

36. The method of claims 34 or 35 which includes providing a computer which receives inputs of bridge unbalance voltage and temperature and solves the algorithm to indicate a moisture content.

37. The method of claims 34 or 35 in which the lowest and highest frequencies differ at least by one power of 10.

38. The method of claim 37 where the lowest frequency is equal to or less than 1 kHz.

39. The method of claim 38 where the highest frequency is equal to or greater than 10 kHz.

40. The method of claims 34 or 35 in which the moisture content is corrected for the particular characteristics of the dielectric material by entering the uncorrected value into the algorithm $$MC_{corr} = k_1 + k_2 MC$$

where $k_1$ and $k_2$ are coefficients unique to the dielectric material being measured.

41. The method of claim 40 in which the dielectric material is wood.

42. The method of claims 34 or 35 including providing two bridge circuits in a balanced push pull arrangement each bridge circuit having a sensing electrode in parallel with a capacitor in one leg of the bridge circuit, each electrode having an adjacent zone within which it is effectively capacitively coupled to the material being measured.

43. The method of claim 42 in which the coupling electrodes are arranged side-by-side in a measuring head.

44. The method of claim 43 including providing a plurality of measurement heads arranged in parallel.

45. In the method of measuring the moisture content of a moisture containing dielectric material by capacitively coupling the material into at least one bridge circuit and measuring the bridge unbalance when an alternating current input having two superposed frequencies is applied across each bridge circuit the improvement which, comprises:
  a. providing a plurality of sensing heads to simultaneously sample the material at a number of different locations, each head having an adjacent sensing zone within which it is effectively coupled to the material being measured,
  b. further providing conveyor means for transporting the material into and out of coupled relationship with the heads,
  c. using a computer to analyze the bridge unbalance signals at each frequency and indicate moisture content, and
  d. determining when the material has moved out of the sensing zone and is no longer effectively coupled to the heads to indicate to the computer that it should reset and await the arrival of a new sample of material.

46. The method of claim 45 which further includes providing a plurality of material detection means in advance of the heads to signal the computer that the material is in position to be fully coupled to any heads which are engaged by the material and to deactivate any heads which are not engaged.

47. The method of claims 45 or 46 which further includes material detection means following the measuring heads to indicate when the material has moved out of the zone in which it is effectively coupled to the heads.

48. The method of claim 47 in which the dielectric material is wood.

* * * * *

UNITED STATES PATENT AND TRADEMARK OFFICE
CERTIFICATE OF CORRECTION

PATENT NO. : 4,580,233
DATED : April 1, 1986
INVENTOR(S) : Robert S. Parker; Frank C. Beall It is certified that error appears in the above—identified patent and that said Letters Patent is hereby corrected as shown below:

In column 10, line 37, "$d=d_0 d_1 T,$" should read --$d=d_0 + d_1 T,$ --

Signed and Sealed this

Nineteenth Day of August 1986

[SEAL]

Attest:

DONALD J. QUIGG

Attesting Officer     Commissioner of Patents and Trademarks